United States Patent [19]

Webb

[11] Patent Number: 4,578,470

[45] Date of Patent: Mar. 25, 1986

[54] BIS-IMIDES CONTAINING HETEROCYCLIC AROMATIC RINGS

[75] Inventor: Jimmy L. Webb, Ballston Lake, N.Y.

[73] Assignee: General Electric Company, Schenectady, N.Y.

[21] Appl. No.: 505,636

[22] Filed: Jun. 20, 1983

[51] Int. Cl.[4] ............................................ C07D 401/14
[52] U.S. Cl. .................................... 546/256; 548/427; 548/465; 548/336; 548/374; 548/193; 548/190; 548/135; 548/138; 548/156; 544/238; 544/296; 544/357; 544/182; 544/212
[58] Field of Search ................ 546/256; 548/427, 465, 548/336, 374, 193, 190, 135, 138, 156; 544/238, 296, 357, 182, 212

[56] References Cited

U.S. PATENT DOCUMENTS 3,933,862  1/1976  Williams .............................. 548/461
4,225,497  9/1980  Baudouin et al. .................... 546/256
4,257,953  3/1981  William, III et al. ............... 548/461
4,273,712  6/1981  William, III ........................ 548/461

OTHER PUBLICATIONS

Williams, C.A. 84: 164473s.
Williams, C.A. 90: 121416g.
Kurita et al., Chem. Abst., vol. 81, 25974f.

Primary Examiner—Jane T. Fan
Attorney, Agent, or Firm—William H. Pittman; James C. Davis, Jr.; James Magee, Jr.

[57] ABSTRACT

Phthalimides and the like in which the substituent on the imide nitrogen is a highly electron-deficient group may be prepared by the reaction of the appropriate amine with phthalic anhydride. These imides are useful for the preparation of polyimides by reaction with diamines.

9 Claims, No Drawings

BIS-IMIDES CONTAINING HETEROCYCLIC AROMATIC RINGS

This invention relates to new imides and their use in polyimide synthesis.

The preparation of polyimides by the reaction of dianhydrides with diamines is known. Illustrative of the polyimides thus prepared are polyetherimides, which have wide utility as engineering plastics. Other homopolymeric and copolymeric polyimides can be prepared from individual diamines and dianhydrides as well as from combinations of various diamines and/or dianhydrides.

Problems are sometimes encountered in polyimide production due to the necessity for preparation of the dianhydride as an intermediate. Typical dianhydrides used for this purpose are collectively designated herein as "bisphenol A dianhydrides" and have the formula

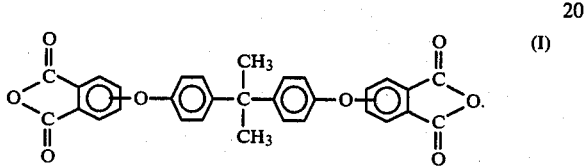

Particularly useful is the compound of formula I wherein the oxy radicals are in the 4-position of the phthalic anhydride ring. This compound is specifically identified hereinafter as "bisphenol A dianhydride". It is typically prepared by an exchange reaction between phthalic anhydride and a corresponding bisimide (hereinafter collectively designated "bisphenol A bisimides"). Reference is made, for example, to the following U.S. Pat. Nos. 4,128,574; 4,329,291; 4,318,857; 4,340,545.

This exchange is an equilibrium reaction and thus it is often somewhat difficult to obtain the desired bisphenol A dianhydride in high yield therefrom. Moreover, the dianhydride must be purified by rather complicated and expensive procedures. Similar problems are frequently encountered with other dianhydrides used in polyimide preparation.

A principal object of the present invention, therefore, is to provide a method for polyimide production which makes unnecessary the use of dianhydrides.

A further object is to provide a relatively easy and inexpensive method for preparing polyimides.

Still another object is to provide new compositions of matter useful as intermediates in polyimide production.

Other objects will in part be obvious and will in part appear hereinafter.

The novel imides of this invention have the formula

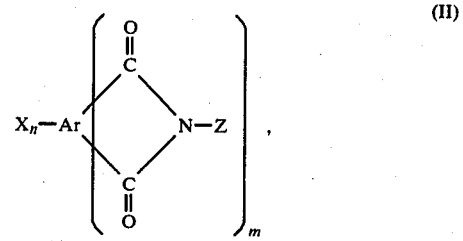

wherein:
Ar is an aromatic radical having adjacent positions substituted by the carbonyl groups of the imide moiety;
X is a substituent;
m is 1 or 2;
n is 0 or 1;
m+n is 2; and
Z is a highly electron-deficient group derived from an amine $Z-NH_2$ which comprises at least 10 mole percent of the free amine constituents of an equilibrated mixture from the following reaction:

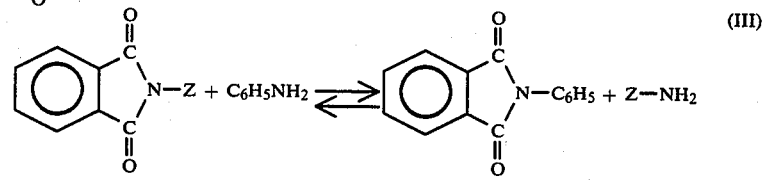

and which, if it comprises less than about 75 mole percent of said free amine constituents, has a boiling point at atmospheric pressure less than about 300° C.

In formula II the Ar moiety may be, for example an o-phenylene, 1,2-naphthylene, 2,3-naphthylene or 1,8-naphthylene radical having an additional free valence bond; it usually has the formula

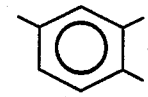

It may be and preferably is unsubstituted other than with the X value, but further substituted radicals wherein the substituents may be, for example, halo, hydroxy, alkoxy, carboxy, carbalkoxy, cyano, nitro, mercapto, alkylthio, alkyl sulfone or the like are within the scope of the invention.

The X value may be any of several substituent groups. For example, it may be a substituent which does not substantially affect the character or reactivity of the imide moiety. Illustrative of such substituents are halogen, OH, $OR^1$, $SR^1$, $SSR^1$, SM, $NO_2$, CN, $COOR^1$,

or $SO_2R^1$. The $R^1$ value therein is an aliphatic or aromatic radical, typically lower alkyl (the word "lower" denoting up to 7 carbon atoms) or a $C_{6-10}$ aryl radical. The M value is an alkali metal, usually lithium, sodium or potassium and preferably sodium. The preferred substituents of this type are Cl, $NO_2$ and SM.

The X value may also have the formula

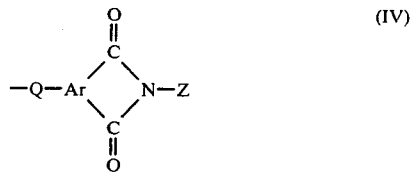

in which Q may be a single bond or a divalent bridging group. The identity of the bridging group is immaterial so long as it does not substantially alter the character or reactivity of the imide moiety. Illustrative bridging groups are —CH$_2$—, —C$_2$H$_4$—, —C(CH$_3$)$_2$—, —O—,

—S$_x$—, —SO$_2$—, —O—R$^2$—O—, —S—R$^2$—S— and —SO$_2$—R$^2$—SO$_2$—, wherein x is 1 or 2 and R$^2$ is a divalent aliphatic or aromatic radical. The preferred bridging group is —O—R$^2$—O— wherein R$^2$ is aromatic. Most preferred as R$^2$ is the radical derived from bisphenol A and having the formula

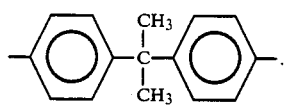

The X moiety may be located in any available position on the Ar radical. When Ar is derived from phthalic acid, the 3- and 4-positions are available: mixtures of 3- and 4-substituted compounds, or exclusively 4-substituted compounds, are then frequently preferred.

Various anhydrides, imides and the like having structures corresponding to those of formula II except for the identity of Z are known in the art. Such compounds in which X is SM or has formula IV wherein Q is —S$_2$— are disclosed and claimed in European published patent application 126,252.

The number of X moieties is designated by the subscript n which may be 0 or 1, and also depends on the value of the subscript m which may be 1 or 2. The compounds included are those in which m+n has the value 2. Thus, it will be apparent that the imides of formula II may be substituted monoimides, bisimides in which all carboxy groups are attached to the same aromatic radical, or bisimides containing two aromatic radicals connected by Q, each of said aromatic radicals also containing an imide moiety. Particularly preferred are the compounds in which m and n are each 1.

The Z value is, as indicated, derived from an amine Z-NH$_2$ which has certain characteristics in the equilibrium reaction represented by equation III. For reasons which will be apparent hereinafter, it is mandatory that said amine comprise at least 10 mole percent of the free amine constituents of an equilibrated mixture from said reaction; that is, at least 10 mole percent of the mixture of said amine and aniline. Most often Z-NH$_2$ will comprise at least about 30 mole percent, and preferably at least about 50 mole percent, of said mixture.

It is also preferred that the amine Z-NH$_2$ have a boiling point at atmospheric pressure less than about 300° C., usually less than 250° C., more preferably less than about 210° C. and most desirably less than 180° C. A maximum boiling point of about 300° C. is mandatory, and the above-noted lower boiling points still more preferred, when said amine comprises less than about 75 mole percent of the free amine constituents of the equilibrated mixture. The lower boiling points are preferred in order that the equilibrium may be easily shifted in favor of polyimide formation during reaction with a diamine as described hereinafter.

Methods for bringing the reaction represented by equation III to equilibrium and analyzing the equilibrated mixture will be apparent to those skilled in the art. In a typical method, a mixture of 0.005 mole each of aniline and the N-(Z-substituted) phthalimide is placed in a 10-ml. stainless steel reactor which is then purged with nitrogen, sealed and heated at 250° C. for one hour in a constant temperature bath. The tube is then removed, cooled and opened and the reaction mixture is sampled and analyzed by high pressure liquid-liquid chromatography.

The principal chemical characteristic of the Z value is its high degree of electron deficiency. For the most part, suitable electron-deficient groups comprise aromatic hydrocarbon radicals containing one or more strongly electron-withdrawing substituents and heterocyclic radicals having aromatic character.

Suitable aromatic hydrocarbon radicals include phenyl, naphthyl and the like containing such substituents as halo, nitro, keto, carbalkoxy, cyano and perfluoroalkyl. At least one of said electron-withdrawing substituents is preferably ortho or para to the free valence bond (i.e., the one attached to the amino group in Z-NH$_2$). The trifluoromethylphenyl radicals are particularly preferred.

Suitable heterocyclic radicals having aromatic character include those with 5- or 6-membered rings and aromatic unsaturation of the type existing in pyrrole and pyridine. These radicals preferably contain 1-3 and especially 1 or 2 hetero atoms of which at least one is nitrogen and the others, if present, are nitrogen or sulfur. They are usually unsubstituted but may be substituted, especially with electron-withdrawing substituents such as those previously enumerated. The free valence bond is preferably in the 2- or 4-position with respect to a hetero atom. If the ring contains more than one hetero atom and especially if it is 5-membered, the free valence bond is preferably attached to the single carbon atom between two of said hetero atoms.

Illustrative 5-membered heterocyclic radicals are pyrrolyl, 2-thiazolyl, 2-imidazolyl and 2-(1,3,4-thiadiazolyl). Illustrative 6-membered radicals are 2-pyridyl, 3-pyridyl, 4-pyridyl, 2-pyrimidyl and 2-pyrazyl. Particularly preferred Z values are the radicals, especially 2-pyridyl and 4-pyridyl.

Some typical amines of the Z-NH$_2$ type are listed in the following table, along with their Z values, equilibrium figures and boiling points when appropriate.

| Amine | Z value | Mole % in equilibrated mixture | B.p., °C. |
|---|---|---|---|
| 2-Aminopyridine | 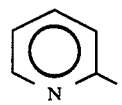 | 95 | — |

-continued

| Amine | Z value | Mole % in equili- brated mixture | B.p., °C. |
|---|---|---|---|
| 3-Aminopyridine | (pyridin-3-yl) | 48.3 | 248 |
| 4-Aminopyridine | (pyridin-4-yl) | 89 | — |
| 2-Amino-5-chloropyridine | (5-chloropyridin-2-yl) | 96.2 | — |
| 2-Amino-5-nitropyridine | (5-nitropyridin-2-yl) | 100 | — |
| 2-Aminopyrimidine | (pyrimidin-2-yl) | 100 | — |
| 2-Aminopyrazine | (pyrazin-2-yl) | 100 | — |
| 2-Aminothiazole | (thiazol-2-yl) | 100 | — |

-continued

| Amine | Z value | Mole % in equili- brated mixture | B.p., °C. |
|---|---|---|---|
| 2-Amino-4-methylthiazole | (4-methylthiazol-2-yl) | 100 | — |
| 2-Aminobenzothiazole | (benzothiazol-2-yl) | 91.3 | — |
| 2-Amino-1,3,4-thiadiazole | (1,3,4-thiadiazol-2-yl) | 100 | — |
| m-Aminobenzotrifluoride | (3-CF$_3$-phenyl) | 56.9 | 187 |

The imides of this invention may be prepared by known methods involving reaction sequences which include the reaction of amines having the formula Z-NH$_2$ with various phthalic acid derivatives such as the free acids, acid halides, anhydrides, diesters or acid esters. The anhydrides are frequently preferred for this purpose because of their availability and relatively low price.

Illustrative reaction sequences for producing various imides of this invention are as follows:

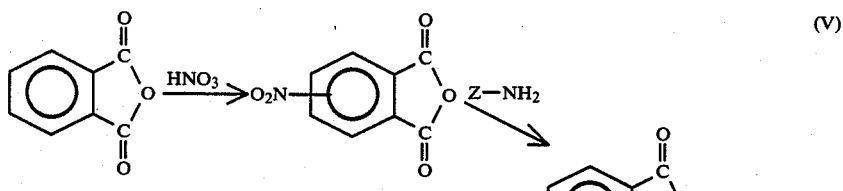

(V)

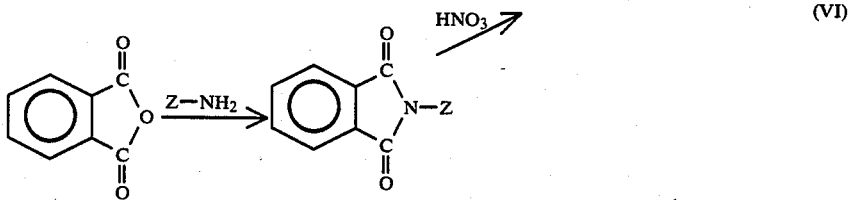

(VI)

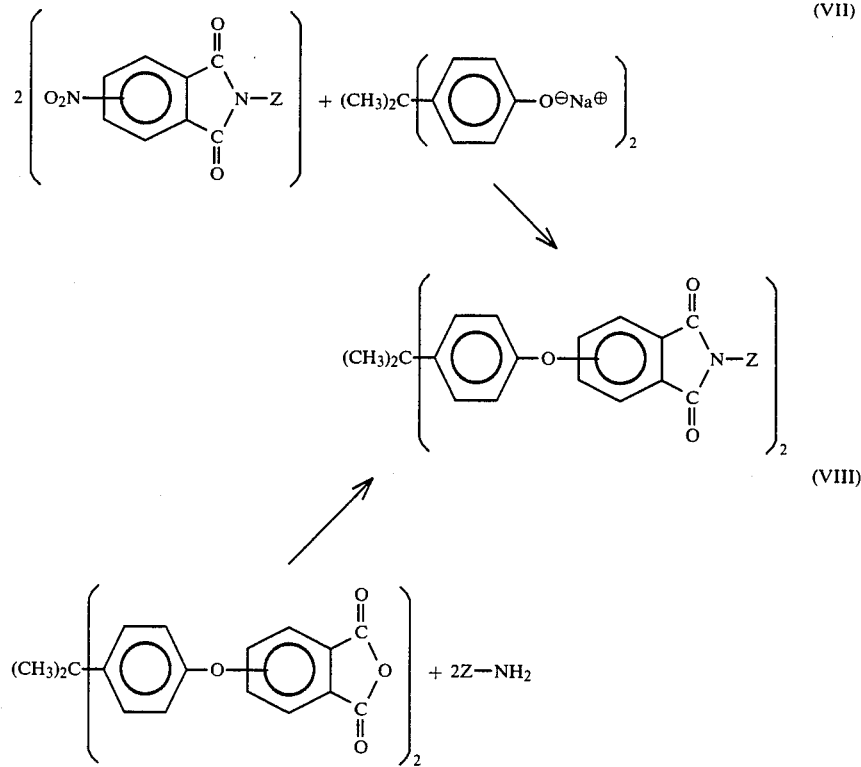

Although the bisphenol A bisimides of this invention can be prepared from the bisphenol A dianhydrides by reaction sequence VIII, it is generally preferred to prepare them from the bisphenol A salt by sequence VII, to avoid preparation of the dianhydride and permit realization of the previously mentioned advantages. Likewise, sequence V is preferred over sequence VI for the preparation of nitrated imides since the intermediate nonnitrated phthalimides in sequence VI are, for the most part, more susceptible to decomposition than phthalic anhydride upon contact with nitric acid.

The anhydride-ZNH₂ reaction may conveniently be effected by merely heating the reactant mixture at a temperature within the range of about 125°–300° C., preferably about 200°–275° C., and removing volatile by-products such as water as they are formed. It is usually preferred to carry out the reaction in an inert atmosphere; e.g., under nitrogen or helium. On some occasions, the use of a substantially inert diluent such as toluene, xylene, chlorobenzene, o-dichlorobenzene, dimethylformamide or dimethyl sulfoxide may be advantageous. In general, approximately equivalent amounts of the phthalic acid derivative and amine are used; e.g., a ratio of equivalents of phthalic acid derivative to amine of about 0.9–1.1:1. When the reaction is complete, the product may be purified if desired by known methods such as recrystallization from a suitable liquid. This reaction scheme may be varied as necessary when a phthalic acid derivative other than the anhydride is used, as will be apparent to those skilled in the art.

The preparation of the imides of this invention is illustrated by the following examples. All parts are by weight.

EXAMPLE 1

A mixture of 5.2 parts (0.01 mole) of bisphenol A dianhydride and 1.88 parts (0.02 mole) of 2-aminopyridine was purged with nitrogen. The reaction vessel was sealed and the mixture was heated at 265° C.; when the mixture melted and water evolution became vigorous, the vessel was vented to the atmosphere to remove water of reaction by evaporation. Evolution of water ceased after about 20 minutes, whereupon the mixture was cooled. There was obtained 6.72 parts of the desired bisphenol A bis-(2-pyridyl)imide as a light yellow solid melting at 225°–226° C.

EXAMPLES 2–6

Following substantially the procedure of Example 1, bisphenol A dianhydride is reacted with equivalent amounts of 4-aminopyridine, 2-aminopyrimidine, 2-aminopyrazine, 2-amino-4-methylthiazole and m-aminobenzotrifluoride, respectively. The corresponding bisimides are obtained.

EXAMPLE 7

By a procedure similar to that of Example 1, equivalent amounts of pyromellitic dianhydride and 2-aminopyridine are reacted to about 200° C. to yield the desired N,N'-bis(2-pyridyl)-pyromellitimide.

EXAMPLE 8

Following substantially the procedure of Example 1, equivalent amounts of 4-chlorophthalic anhydride and 2-aminopyrimidine are reacted at 200° C. to yield the desired 4-chloro-(2-pyrimidyl)-phthalimide.

EXAMPLE 9

A solution of 0.00256 mole each of 4-chloro-N-(2-pyrimidyl)-phthalimide and sodium sulfide in 20 ml. of dimethylformamide is heated at 125° C., with stirring, in a nitrogen atmosphere for 1 hour. The product obtained thereby is a solution in dimethylformamide of the desired sodium 4-[N-(2-pyrimidyl)phthalimide]sulfide.

EXAMPLE 10

To the solution prepared by the method of Example 9 is added an equivalent amount (i.e., 0.00128 mole) of ethylene dibromide. The mixture is heated for 1 hour at 100° C., with stirring, and poured into water. The desired ethylene 1,2-bis[4-N-(2-pyrimidyl)-phthalimide sulfide] is separated by filtration and dried.

The imides of this invention are useful as intermediates for the preparation of polyimides, and another embodiment of the invention is a method for preparing a polyimide which comprises reacting at least one diamine with at least one bisimide according to the invention. The monoimides of the invention may be used in the preparation of bisimides by various reactions known in the art; e.g., the nitro imides may be reacted with the disodium salt of bisphenol A according to reaction sequence VII to give the corresponding bisphenol A bisimides. The monoimides may also be used as chain stopping agents in polyimide formation, by incorporation with bisimides in the reaction mixture.

Examples of suitable diamines for polyimide preparation are ethylenediamine, propylenediamine, trimethylenediamine, diethylenetriamine, triethylenetetramine, heptamethylenediamine, octamethylenediamine, 2,11-dodecanediamine, 1,12-octadecanediamine, 3-methylheptamethylenediamine, 4,4-dimethylheptamethylenediamine, 4-methylnonamethylenediamine, 2,5-dimethylhexamethylenediamine, 2,2-dimethylpropylenediamine, N-methyl-bis(3-aminopropyl)amine, 3-methoxyhexamethylenediamine, 1,2-bis(3-aminopropoxy)ethane, bis(3-aminopropyl)sulfide, 1,4-cyclohexanediamine, bis-(4-aminocyclohexyl)methane, m-phenylenediamine, p-phenylenediamine, 2,4-diaminotoluene, 2,6-diaminotoluene, m-xylylenediamine, p-xylylenediamine, benzidine, 3,3'-dimethylbenzidine, 3,3'-dimethoxybenzidine, 1,5-diaminonaphthalene, 4,4'-diaminodiphenylmethane, 4,4'-diaminoiphenylpropane, 2,4-bis-(β-amino-t-butyl)toluene, bis(p-β-methylo-aminopentyl)-benzene, 1,3-diamino-4-isopropylbenzene, 4,4'-diaminodiphenyl sulfone, 4,4'-diaminodiphenyl ether and bis(3-aminopropyl) tetramethyldisiloxane. Mixtures of these diamines may also be used. Particularly preferred are the aromatic diamines, especially m-phenylenediamine and 4,4'-diaminodiphenylmethane.

The polyimides may be prepared by merely heating the bisimide-diamine mixture, typically with agitation and at a temperature in the range of about 100°–250° C., preferably about 225°–350° C. and most desirably about 250°–325° C. In general, substantially equimolar amounts of diamine and bisimide are used for high molecular weight polyimides, with typical mole ratios of bisimide to diamine being about 0.95–1.05:1. Molecular weight control may be effected by adding organic monoamines or organic monoimides, including the monoimides of this invention as noted hereinabove, typically in amounts of 5 mole percent or less based on the bisimide-diamine combination. Polyimide formation may be effected by a melt polymerization procedure or inert diluents such as toluene, xylene, m-cresol or o-dichlorobenzene (or combinations thereof) may be employed.

Polyimide formation by the method of this invention is an equilibrium reaction and is analogous to reaction III, since the reactivities of the aromatic an aliphatic diamines therein are, respectively, comparable to and usually greater than that of aniline. Therefore, it is promoted by removal of the amine Z-NH$_2$. Removal by distillation by or purging with an inert gas (e.g., nitrogen) is frequently effective, especially when the boiling point of said amine is relatively low. When the amine is one for which the equilibrium is particularly favorable, it may be possible to isolate the polyimide by precipitation or the like; e.g., by adding a nonsolvent therefor. In any event, said amine may be recycled if desired to produce the imides of this invention.

The preparation of polyimides according to the method of this invention is illustrated by the following example.

EXAMPLE 11

A mixture of 3.4 parts (0.00505 mole) of the bisimide of Example 1 and 0.05492 part (0.00505 mole) of m-phenylenediamine was purged with nitrogen, sealed and heated at 270° C.; the later stages of the reaction were effected at a reduced pressure of about 25 torr. The temperature was then raised slowly to 315° C. and the reaction was continued for a total of about 1 hour. The desired polyimide was obtained as a light yellow solid. It had a weight average molecular weight of about 156,000 and an intrinsic viscosity of 0.763 dl./g. in chloroform at 25° C.

The polyimides of this invention have uses similar or identical to those of the corresponding polyimides prepared by the reaction of dianhydrides with diamines. Thus, they may be used for the formation of films, molding compounds, coating and the like. Typical areas of utility are in automobile and aviation applications for decorative and protective purposes, as high temperature electrical insulators and dielectric capacitors, as coil and cable wrappings, for containers and container linings, in laminating structures for application as films to various heat-resistant or other types of materials, and as filled compositions where the fillers may be asbestos, mica, glass fiber or the like. Other uses include as binders for asbestos fibers, carbon fibers and other fibrous materials making brake linings, and for formulation of molding compositions using fillers such as asbestos, glass fibers, talc, quartz, wood flour, finely divided carbon and silica. Other uses for polyimides are described in a large number of United States patents.

What is claimed is:

1. A bisimide having the formula

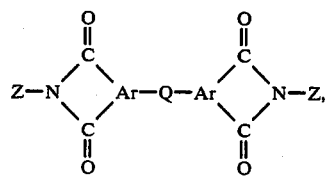

wherein:

Ar is a trivalent benzene or naphthalene radical having adjacent positions substituted by the carbonyl groups of the imide moiety;

Q is a single bond, —CH₂—, —C₂H₄—, —C(CH₃)₂—, —O—,

—S$_x$—, —SO₂— or

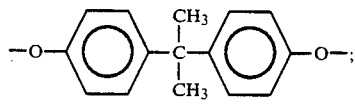

Z is a highly electron-deficient heterocyclic group having a 5- or 6-membered ring and aromatic unsaturation and containing 1-3 hetero atoms of which at least one is nitrogen and the others, if present, are nitrogen or sulfur; and
x is 1 or 2.

2. A bisimide according to claim 1 wherein the amine Z-NH₂ has a boiling point at atmospheric pressure less than 250° C.

3. A bisimide according to claim 2 wherein Q is

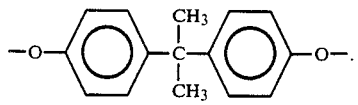

4. A bisimide according to claim 3 wherein Ar has the formula

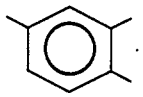

5. A bisimide according to claim 2 wherein Z has a 6-membered ring and the free valence bond is in the 2- or 4-position.

6. A bisimide having the formula

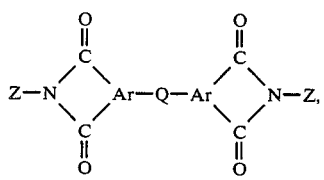

wherein:
Ar is a trivalent benzene or naphthalene radical having adjacent positions substituted by the carbonyl groups of the imide moiety;

Q is a single bond, —CH₂—, —C₂H₄—, —C(CH₃)₂—, —O—,

—S$_x$—, —SO₂— or

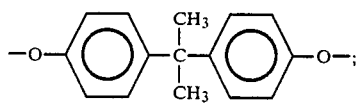

Z is an unsubstituted or halo- or nitro-substituted 2-pyridyl, 3-pyridyl, 4-pyridyl, 2-pyrimidyl or 2-pyrazyl radical; and
x is 1 or 2.

7. A bisimide according to claim 6 wherein Z is 2-pyridyl or 4-pyridyl.

8. A bisimide according to claim 2 wherein Z has a 5-membered ring and two hetero atoms, and the free valence bond is attached to the single carbon atom between hetero atoms.

9. A bisimide having the formula

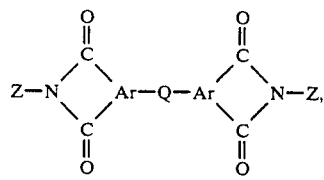

wherein:
Ar is a trivalent benzene or naphthalene radical having adjacent positions substituted by the carbonyl groups of the imide moiety;
Q is a single bond, —CH₂—, —C₂H₄—, —C(CH₃)₂—, —O—,

—S$_x$—, —SO₂— or

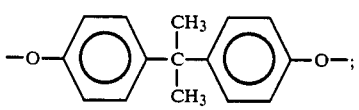

Z is an unsubstituted or methyl- or benzo-substituted 2-thiazolyl or 2-(1,3,5-thiadiazolyl) radical; and
x is 1 or 2.

* * * * *